United States Patent [19]

Givens

[11] Patent Number: 4,926,128
[45] Date of Patent: May 15, 1990

[54] METHOD FOR UTILIZING MEASURED RESISTIVITIES OF POROUS ROCK UNDER DIFFERING FLUID SATURATIONS TO IDENTIFY FLUID DISTRIBUTION EQUILIBRIUM

[75] Inventor: Wyatt W. Givens, Dallas, Tex.

[73] Assignee: Mobil Oil Corporation, New York, N.Y.

[21] Appl. No.: 309,754

[22] Filed: Feb. 13, 1989

[51] Int. Cl.$^5$ .............................................. G01V 3/02
[52] U.S. Cl. ..................................................... 324/376
[58] Field of Search ...................... 324/376, 377, 71.1, 324/448, 446, 323, 65 P, 61 R, 65 R

[56] References Cited

U.S. PATENT DOCUMENTS

| | | |
|---|---|---|
| 3,302,101 | 1/1967 | Glauville ............................ 324/376 |
| 3,839,899 | 10/1974 | McMillen . |
| 3,982,177 | 9/1976 | Walker et al. ...................... 324/376 |
| 4,379,407 | 4/1983 | Masse et al. . |
| 4,380,903 | 4/1983 | Podhransky et al. . |
| 4,467,642 | 8/1984 | Givens . |
| 4,486,714 | 12/1984 | Davis, Jr. et al. ................. 324/376 |
| 4,543,821 | 10/1985 | Davis, Jr. ........................ 324/376 X |
| 4,546,318 | 10/1985 | Bowden . |
| 4,628,267 | 12/1986 | Lee et al. ............................ 324/376 |
| 4,644,283 | 2/1987 | Vinegar et al. ..................... 324/376 |
| 4,646,000 | 2/1987 | Wills ............................... 324/376 X |
| 4,686,477 | 8/1987 | Givens et al. . |
| 4,688,238 | 8/1987 | Sprunt et al. . |

FOREIGN PATENT DOCUMENTS 510561 3/1955 Canada ................................ 324/376

Primary Examiner—Reinhard J. Eisenzopf
Assistant Examiner—Warren S. Edmonds
Attorney, Agent, or Firm—Alexander J. McKillop; Charles J. Speciale; George W. Hager, Jr.

[57] ABSTRACT

Resistivities are measured for a plurality of subsections of a porous rock following a fluid injection that alters the fluid saturation throughout the porous rock. The measured subsection resistivites are compared to identify an equilibrium in the altered fluid saturation throughout the porous rock when there is a fixed relationship between the measured subsection resistivities. Following the detection of fluid saturation equilibrium, the resistivity of the porous rock is measured.

5 Claims, 3 Drawing Sheets

METHOD FOR UTILIZING MEASURED RESISTIVITIES OF POROUS ROCK UNDER DIFFERING FLUID SATURATIONS TO IDENTIFY FLUID DISTRIBUTION EQUILIBRIUM

BACKGROUND OF THE INVENTION

This invention relates to the area of oil and natural gas exploration and, more particularly, to a method for identifying regions of rock formations having significant water saturations from which hydrocarbons may be produced without significant attendant water production.

Subsurface reservoirs of natural gas and petroleum, hereinafter referred to generically as "hydrocarbons" are typically found trapped in permeable geological strata beneath a layer of impermeable strata material. A hydrocarbon will "float" upon any ground water present although typically, a transition zone will exist between the two fluids due to the water being raised by capillary action of the permeable strata material. In some regions, impermeable layers may be relatively closely stacked atop one another trapping thin zones of what may be essentially hydrocarbons, essentially water or mixed hydrocarbons and water. A well bore dropped through the formation and various layers may produce water if tapped in a transition region or mixed hydrocarbon and water zone. The cost of transporting, separating and disposing of the attendant water adds sufficiently to production costs that hydrocarbon reservoirs have often been left untapped where it is expected or believed they would produce an excessive amount of attendant water.

Water saturation present at various levels of a formation is typically determined from interpretation of conventional electrical (i.e., resistivity) logs taken through a borehole dropped through the formation. Water saturation of the available pore space of the formation is determined from the resistivity log measurements using the Archie equation set forth in "The Electrical Resistivity Log As An Aid In Determining Some Reservoir Characteristics", Trans. AIME, Vol. 46, pp. 54–62, 1942, by G. E. Archie. This equation is expressed as follows:

$$S_w{}^n = R_w/\phi^m R_S \tag{1}$$

Where "$S_w$" is the fractional water saturation (i.e. free and bound water of the formation expressed as a percent of the available pore space of the formation), "$R_w$" is the formation water resistivity, "$\phi$" is the of formation porosity, "$R_t$" is the formation resistivity indicated by the resistivity log, "n" is the saturation exponent and "m" is the porosity or cementation exponent. The Archie equation may be expressed in other ways and there are numerous methods in the art for determining, measuring or otherwise obtaining the various components needed to predict fractional water saturation $S_w$ from the log-indicated resistivity, $R_t$, using the equation in any of its forms.

Archie defined two quantities that provided the basis for his water saturation equation (1). The first quantity is the formation factor F which defines the effect of the rock matrix on the resistivity of water as follows:

$$F = R_o/R_w \tag{2}$$

where

Ro = resistivity of water saturated rock and
Rw = water resistivity.

Archie reasoned that for a given value of Rw, the formation factor F would decrease with increasing porosity, $\phi$, to some exponent m:

$$F = 1/\phi^m \tag{3}$$

This porosity exponent m has also become known as the cementation exponent. Thus Archie provided a useful characterization of a rock fully saturated with a conducting brine in terms of the water resistivity Rw, porosity $\phi$ and a rock parameter m. It is important to note that Archie assumed all conductance to be in the brine.

The second quantity is the resistivity index I defined as the ratio of the resistivity of a rock partially saturated with water and hydrocarbon $R_t$, to the same rock saturated fully with water, Ro, as follows:

$$I = R_t R_o \tag{4}$$

Archie reasoned that as the water saturation decreased (i.e. hydrocarbon saturation increased) the resistivity $R_t$ and hence I would increase to some exponent n:

$$I = 1/S_w{}^n \tag{5}$$

where Sw = volume of water in pores/total pore volume. This exponent n has become known as the saturation exponent. It is again important to note that Archie assumed all conductance to be in the brine and further that all pores within the rock have the same water saturation Sw.

It is these two equations (3) and (5) for the formation factor F and resistivity index I respectively that Archie combined to provide the water saturation expression Sw of equation (1). Certain logs provide porosity $\phi$, water samples provide the best values for Rw, and the cementation exponent m and saturation exponent n are obtained by electrical measurements on core samples.

Standard practice is to measure rock sample resistivities $R_o$ and $R_t$ for a number of water saturations and to plot the logarithm of I versus the logarithm of Sw. Such a logarithmic plot is a straight line with slope of -n. This plot, however, assumes that all rock pores are desaturated equally, all resistivities for partial water saturation are measured under equilibrium saturation conditions throughout the rock sample, and all conductance is in the brine. If water saturation has not reached equilibrium throughout the rock sample, then the value of the measured resistivity index I will not be correct and therefore the value of the saturation exponent n will not be the value of n that is characteristic of the rock. It is therefore the specific objective of the present invention to provide a method for measuring the saturation equilibrium conditions of a porous rock sample, so that the true value of the saturation exponent n may be determined. Present methods cannot make such an identification, but merely rely on waiting periods after each new partial water saturation is effected in the rock sample over which it is assumed that an equilibrium condition has been reached so that a resistivity measurement can be made.

SUMMARY OF THE INVENTION

In accordance with the present invention, a method is provided for identifying fluid distribution equilibrium in porous rock following a change in the electrically conducting fluid saturation throughout the rock so that rock resistivity can then be determined.

In one aspect, the fluid distribution equilibrium in a porous rock is measured following a change in the electrically conducting fluid saturation within the roCk. Measured subsection resistivities are compared to identify an equilibrium in the fluid distribution of an electrically conducting fluid and an immiscible non-conducting fluid throughout the porous rock when there is a fixed relationship between these measured subsection resistivities. Following the detection of fluid distribution equilibrium, the resistivity of the porous rock is measured.

In a more specific aspect, the resistivity of a porous rock is measured for each of a plurality of differing fluid saturations throughout the porous rock. In a first step, a first fluid is injected into a core sample of a porous rock to effect a first fluid saturation, preferably complete fluid saturation, throughout the core sample. The resistivity along a selected length of the core sample is made for this saturation. In a second step, an immiscible and oppositely conducting fluid is "injected" into an end of the core sample at an injection pressure to displace a portion of the first fluid from the sample, thereby effecting a second first fluid saturation which is a partial saturation with respect to the first fluid saturation. Resistivities are measured for a plurality of subsections along the selected length of core sample while maintaining the second fluid injection pressure. Those measured subsection resistivities are compared to detect the occurrence of an equilibrium in the distribution of the first and second fluids within the core sample at the partial first fluid saturation. The resistivity is again measured along the selected length of the core sample upon the detection of such an equilibrium. This second step is repeated for a plurality of successively increased injection pressures for the second fluid to effect a plurality of resistivity measurements at successively decreased partial first fluid saturations within the core sample.

In a more specific aspect, the comparison of the measured resistivities of the subsections of the core sample includes the determination of resistivity gradients between select ones of the subsections. The distribution of the first and second fluids within the core sample is determined to be in equilibrium when each of the measured resistivity gradients becomes zero, particularly when the porous rock is homogenous.

In another aspect, the comparison of the measured resistivities of the subsections of the core sample includes the determination of resistivity of selected pairs of the measured resistivities. The distribution of the first and second fluids within the core sample is determined to be in equilibrium when each of the resistivity ratios becomes constant, particularly when the porous rock is heterogenous.

In further aspect, ratios are determined of the measured resistivities along the selected length of core sample at equilibrium for each of the plurality of second partial first fluid saturations to the measured resistivity along the selected length of core sample at equilibrium for the first fluid saturation. These ratios are recorded along with the corresponding partial first fluid saturations for which they were determined. Preferably this recording includes the logarithmic plotting of the ratios against the corresponding partial first fluid saturations.

In a yet further aspect, the resistivity measurements of the plurality of subsections of core sample is carried out by positioning a plurality of electrodes along the select length of core sample, the spacings between the electrodes defining the subsections. The lengths and cross sectional areas of the subsections are determined. A current is passed through the select length of core sample. The voltage between each adjacent pair of electrodes is measured. The resistivity of each subsection is determined from the measured voltage across the subsection, the current through the subsection and the length and cross sectional area of the subsection. These subsection resistivities are compared for a homogenous rock by subtracting the resistivities of adjacent pairs of subsections to determine a resistivity gradient between each of the pairs of subsections and equilibrium is identified in the distribution of the first and second fluids within the core sample when the resistivity gradient between each pair of subsections is zero. Alternatively, the subsection resistivities are compared for a heterogenous rock by determining the ratio of measured resistivities of adjacent pairs of subsections and equilibrium is identified in the distribution of the first and second fluids within the core sample when each of the measured resistivities of adjacent pairs of subsections is a constant.

In a still further aspect the electrically conducting fluid is a salt water, preferably brine, and the immiscible non-conducting fluid is a hydrocarbon, preferably oil.

DESCRIPTION OF THE PREFERRED EMBODIMENT

Figure 1:
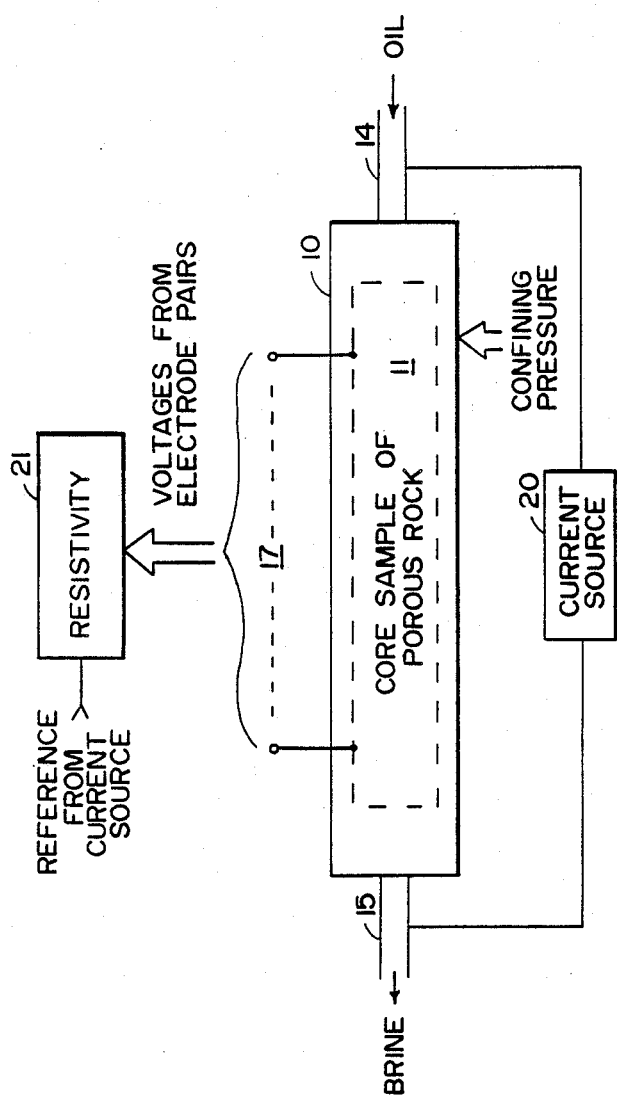
FIGS. 1 and 2 illustrate apparatus in which a core sample of a porous rock may be placed in the carrying out of resistivity measurements for a plurality of partial water saturation conditions.
Figure 2:
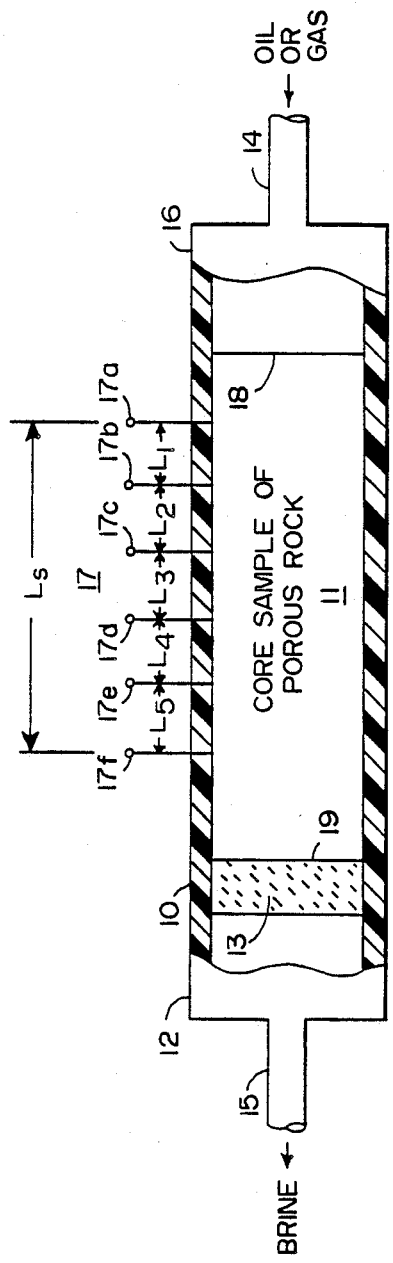

The method of the present invention of desaturating a porous rock through a plurality of partial fluid saturations and making resistivity measurements at each such partial fluid saturation to identify fluid distribution equilibrium may preferably be carried out with the apparatus shown in FIGS. 1 and 2. A pressure sleeve 10, preferably natural or synthetic rubber, is in the form of a cylinder surrounding a core sample 11 of a porous rock to be measured for resistivity at a plurality of fluid saturations. Positioned between the core sample 11 and end 12 of the pressure sleeve 10 as shown in FIG. 2 is a porous member 13, which is permeable to a first fluid saturating the core sample, but is impermeable to a second fluid used to displace the first fluid from the core sample. The second, or displacing fluid, is immiscible with the first fluid saturating the core sample and is of opposite electrical conductivity. This first saturation fluid is the wetting fluid for the porous member 13, which by way of example, may be a ceramic plate or a membrane, such as oil or gas, up to very high injection pressures. Sleeve 10 is placed inside a suitable pressure vessel (not shown) that can be pressurized up to several thousand pounds per square inch. Typical of such pressure vessels are those described in U.S. Pat. Nos. 3,839,899 to McMillan, 4,688,238 to Sprunt et al; and 4,379,407 to Masse et al. Through such a pressure vessel a pressure is applied to the sleeve 10 and hence to the porous rock 11. A fluid inlet 14 and a fluid outlet 15 feed into the ends 16 and 12 respectively of the sleeve 10.

Both inlet 14 and outlet 15 also serve as current conducting electrodes for passing current from a source 20 through the porous rock 11 when it contains a sufficient amount of electrically conducting fluid. A plurality of voltage electrodes 17 pentrate sleeve 10 and make a contact with the porous rock at a plurality of spaced locations along the length of the porous rock.

In carrying out the method of the present invention with such apparatus of FIGS. 1 and 2, a core sample of a porous rock 11 is initially fully saturated, by way of example, with an electrically conducting fluid, such as salt water, preferably brine, and placed within sleeve 10 under confining pressure. A current is passed through the porous rock at this initial saturation condition and the voltage $V_s$ along the length $L_s$ of the porous rock is measured between electrodes 17a and 17f. As noted above, the inlet 14 and outlet 15 function as current electrodes conducting current into and out of porous rock while the brine acts as the conducting medium within the porous rock and the porous member 13. Such voltage measurements, as well as later voltage measurements described below, may be carried out in accordance with the teachings of U.S. Pat. No. 4,467,642 to Givens., U.S. Pat. No. 4,546,318 to Bowden and U.S. Pat. No. 4,686,477 to Givens et al, the teachings of which are incorporated herein by reference. From this voltage $V_s$ the resistance $r_s$ of the porous rock along the length $L_s$ is determined using Ohm's Law by the resistance section of the resistivity unit 21. The resistivity unit 21 calculates the resistivity $R_s$ using the resistance $r_s$, the length $L_s$ and the cross-sectional area of the core $A_c$. (Note $R_s = r_s A_c / L_s$) A nonconducting fluid displacing liquid such as a hydrocarbon, preferably oil, is then forced through inlet 14 into end 18 of porous rock 11 under a pressure $P_1$. It takes a finite amount of time for the oil to pass through the porous rock displacing brine through a brine permeable and oil impermeable porous member 13 and hence through outlet 15. Initially only fingers of oil travel through the porous rock 11 from end 18 toward end 19. This can be thought of as an oil front. There is therefore initially a definite disequilibrium in the distribution of the brine and oil throughout the porous rock. After an interval of time under pressure $P_1$, such fluid distribution reaches a state of equilibrium throughout the porous rock. The interval of time depends on a number of rock and fluid properties, such as permeability of the rock to brine and oil, length of the core sample of the porous rock, viscosity of the oil, and pore geometry among others.

It is a specific feature of the present invention to determine when this state of equilibrium has been reached under injection pressure $P_1$ so that a resistivity measurement can be made on porous rock for the saturation condition existing at that time. This determination is made by measuring the voltage between each of the pairs of adjacent electrodes 17 and comparing these measured voltages to identify when the fluid distribution of the brine and oil is no longer changing following the oil injection at such pressure $P_1$. More particularly, the electrodes 17 are spaced-apart by the distances $L_1-L_5$ along the length $L_s$ of the porous rock, thereby dividing the porous rock into a plurality of subsections having the lengths $L_1-L_5$. The voltage across each of these subsection lengths, that is $V_1-V_5$, is measured and resistivities $R_1-R_5$ determined by the resistivity unit 21 from Ohm's Law, the lengths $L_1$ through $L_5$ and the cross-sectional area of the core $A_c$ in response to the passage of the current through the porous rock.

By comparing these resistivity determinations, the occurrence of fluid saturation equilibrium at total water saturation and at an injection pressure $P_1$ can be identified. This comparison is carried out in one of two ways depending upon whether the porous rock is homogenous or heterogenous. Measurements are first made with the rock fully brine saturated, before an oil is injected, to obtain resistivity $R_{os}$ determinations along the rock (e.g. $R_{01}$, $R_{02}$, $R_{03}$, etc). If these resistivities are all equal, the rock is homogenous. If there are resistivity gradients indicated by the ratios $R_{01}/R_{02}$, $R_{02}/R_{03}$, etc., the rock is heterogenous.

Firstly, this comparison will be described for a homogenous porous rock and then for a heterogenous porous rock. As oil enters a homogenous porous rock through inlet 14 it passes the plane of electrode 17a through the porous rock, enters the subsection of the porous rock between electrodes 17a and 17b and changes the fluid distribution of the brine and oil between electrodes 17a and 17b. At this point in time the voltage measurement $V_1$ across subsection length $L_1$ will be greater than voltage measurements $V_2-V_5$ across subsection lengths $L_2-L_5$, hence the resistivity $R_1$ will be greater than resistivities $R_2-R_5$. It doesn't matter whether the lengths $L_1-L_5$ of the subsections are equal or not since any variations in such length only affects the resistances of the subsections and not the resistivities for a uniform and homogenous porous rock.

As the oil progresses through the porous rock toward the porous plate 13 at the opposite end 19 of the porous rock, the fluid saturations between each additional pair of electrodes 17 progressively change according to the oil and brine distribution within the subsections between the electrodes, hence the corresponding subsection resistivities progressively change also. After some interval of time, the oil will reach the porous member 13 under injection pressure $P_1$. As long as injection pressure $P_1$ is less than a critical breakthrough pressure of the porous member 12, the oil will not penetrate the porous member 13. At this point the oil fingers established throughout the porous rock begin to enlarge with such enlargement traveling in the reverse direction from the end 19 adjacent the porous member 13 toward the end 18 adjacent the injection inlet 14. In time fluid saturation equilibrium is established and the oil fingers swell essentially equally throughout the length of the porous rock until all the brine that can be displaced from porous rock at injection pressure $P_1$ is displaced from end 19 through porous member 13. For the homogenous porous rock there is now resistivity equilibrium, that is, there are no resistivity gradients along the length of the porous rock since all resistivities $R_1-R_5$ are equal. Upon identification of fluid saturation equilibrium at injection pressure $P_1$ from a comparison of $R_1-R_5$, the foregoing described procedure is repeated for a plurality of incrementally increased oil injection pressures to provide a plurality of resistivity determinations $R_s$ at fluid saturation equilibrium for a corresponding plurality of partial water saturations within the porous rock such that resistivity indexes I can be plotted against water saturation to obtain the Archie saturation exponent n.

Having now described the comparison of determined resistivities for a homogenous porous rock to identify fluid saturation equilibrium, a comparison of the same resistivities for a heterogenous porous rock will now be described. In a heterogenous porous rock, as contrasted with a homogenous porous rock, certain rock charac- teristics, such as porosity and pore size among others, vary through the length of the porous rock. Resistivity determinations as described above at various oil injection pressures, and hence various water saturations will not be equal between the porous rock subsections at a fluid saturation equilibrium for the heterogenous porous rock. Resistivities of some subsections might be equal, but others will not. Consequently, a comparison of such resistivities on the basis of resistivity gradients will not identify fluid saturation equilibrium as in the case of the homogenous porous rock. A different type of comparison is required. Such a comparison involves determining the ratios of resistivities between pairs of electrodes 17 and identifying fluid saturation equilibrium when each of such ratios becomes a constant. This can best be seen by again referring to the fluid distribution existing in the heterogenous porous rock as described above for the homogenous porous rock at total water saturation and at an initial oil injection pressure $P_1$. As the oil fingers through the porous rock the resistivities across subsections of lengths $L_1$-$L_5$ will not be equal. Consequently the ratios K of pairs of such resistivities will likewise not be equal. Further, the value of only such ratio K will be changing until such time as fluid saturation equilibrium is established in both the subsections of the porous rock for which the ratio K has been determined. At such point of fluid saturation equilibrium between a given pair of subsections the ratio K will thereafter remain constant. Accordingly, fluid saturation equilibrium of the porous rock across the entire length $L_s$ can be identified when the ratios of resistivities between each pair of subsections of the porous rock all become constant, but not equal.

Figure 3:
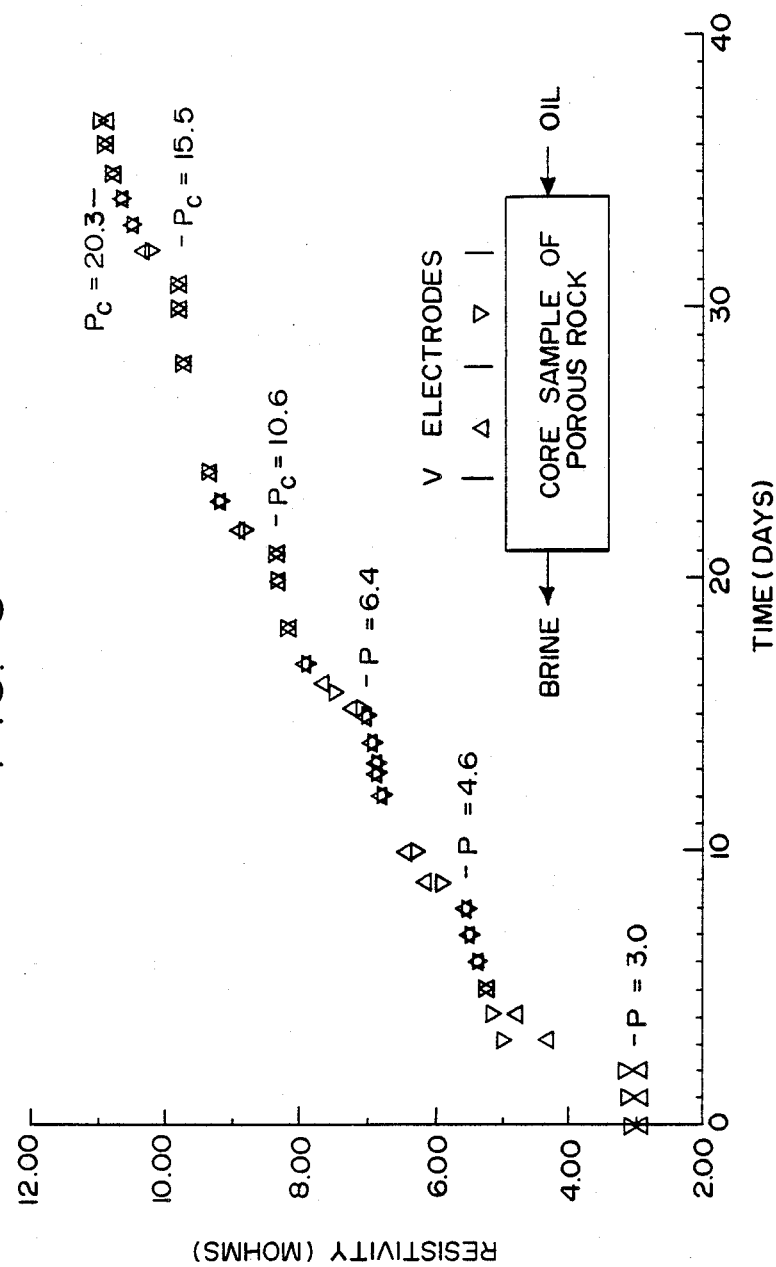
FIG. 3 shows resistivity measurements on a core sample of a homogenous porous rock made with the apparatus of FIGS. 1 and 2 in accordance with the teaching of the present invention.

Having now described the method of the present invention as carried out on both homogenous and heterogenous porous rocks under conditions of the above described example of oil displacing brine within the core sample, an example of the comparison of resistivities determined between two pairs of electrodes for a homogenous porous rock is shown in FIG. 3. The value of determined resistivity is plotted against time for the two pairs of electrodes illustrated. Injection pressure ($P_c$) changes are also shown. It took 3 to 4 days for fluid saturation equilibrium to be reached after each incremental pressure increase for the homogenous porous rock being examined. Since prior practice is to make a resistivity measurement across the length of a porous rock in a few hours after each incremental injection pressure change, it can clearly be seen that any value of the saturation exponent 1 derived from such resistivities will not be representative of the actual or true saturation exponent for that particular porous rock. By carrying out the method of the present invention, the point in time when fluid saturation equilibrium does occur is identified precisely so that a resistivity measurement across the length of the porous rock can be timely made and used to derive the true value of the saturation exponent for the particular porous rock being examined, whether it be homogenous or heterogenous.

The method of the present invention has been described in conjunction with the above example of a core sample saturated with a conducting fluid, such as brine, and a non-conducting displacing fluid, such as oil. This fluid displacement can be referred to as a drainage cycle. However, the method of the present invention can also be carried out by firstly saturating the core sample with a non-conducting fluid, such as oil, and then displacing such oil with a conducting fluid, such as brine. This fluid displacement can be referred to as a imbibition cycle. Consequently the method of the present invention may be used for measuring fluid distribution equilibrium of two immiscible and oppositely conducting fluids for either a drainage or an imbibition cycle, or any repetitive sequencing thereof.

While the foregoing has described a preferred embodiment of the method of the present invention, it is to be understood that various modifications or changes may be made without departing from the spirit and scope of the present invention as set forth in the appended claims.

What is claimed is:

1. A method for measuring the fluid distribution equilibrium of a porous rock comprising the steps of:
    (a) injecting a first fluid into a porous rock to effect a first fluid saturation throughout said porous rock,
    (b) measuring resistivity along a selected length of said porous rock at said first fluid saturation,
    (c) injecting a second fluid which is immiscible with and of opposite electrical conductance with said first fluid into an end of said porous rock at an injection pressure to displace a portion of said first fluid from said porous rock and thereby effect a fluid saturation within said porous rock which is a partial saturation with respect to said first fluid saturation,
    (d) measuring resistivities of a plurality of subsections along said selected length of porous rock while maintaining said injection pressure,
    (e) determining resistivity gradients between select ones of said measured resistivities, and
    (f) determining the distribution of said first and second fluids within said porous rock to be in equilibrium when each of said measured resistivity gradients becomes zero.

2. The method of claim 1 wherein said steps are carried out on a homogenous porous rock.

3. A method for measuring the fluid distribution equilibrium of a porous rock comprising the steps of:
    (a) injecting a first fluid into a porous rock to effect a first fluid saturation throughout said porous rock,
    (b) measuring resistivity along a selected length of said porous rock at said first fluid saturation,
    (c) injecting a second fluid which is immiscible with and of opposite electrical conductance with said first fluid into an end of said porous rock at an injection pressure to displace a portion of said first fluid from said porous rock and thereby effect a fluid saturation within said porous rock which is a partial saturation with respect to said first fluid saturation,
    (d) measuring resistivities of a plurality of subsections along said selected length of porous rock while maintaining said injection pressure,
    (e) comparing the measured resistivities of said subsections to detect the occurrence of an equilibrium in the distribution of said first and second fluids throughout said porous rock,
    (f) measuring resistivity along said selected length of porous rock upon the detection of equilibrium in the distribution of said first and second fluids,
    (g) repeating steps (c) and (f) for a plurality of successively increased injection pressures for said second fluid to effect a plurality of resistivity measurements at successively decreased first fluid saturations throughout said porous rock, (h) determining the ratios of each of said measured resistivities along the selected length of said porous rock from each repetition of step (f) to the measured resistivity along the selected length of said porous rock of step (b), and (i) recording said ratios with the corresponding fluid saturations at which the measured resistivities of step (f) were carried out by the logarithmic plotting of said ratios against the corresponding first fluid saturations.

4. A method for measuring the fluid distribution equilibrium of a porous rock comprising the steps of:

(a) injecting a first fluid into a porous rock to effect a first fluid saturation throughout that is a complete fluid saturation of said porous rock with said first fluid saturation, (b) measuring resistivity along a selected length of said porous rock at said first fluid saturation, (c) injecting a second fluid which is immiscible with and of opposite electrical conductance with said first fluid into an end of said porous rock at an injection pressure to displace a portion of said first fluid from said porous rock and thereby effect a second fluid saturation within said porous rock which is a partial saturation with respect to said first fluid saturation, (d) measuring resistivities of a plurality of subsections along said selected length of porous rock while maintaining said injection pressure, (e) comparing the measured resistivities of said subsections to detect the occurrence of an equilibrium in the distribution of said first and second fluids throughout said porous rock, (f) repeating steps (c) through (e) at successively increased injection pressures to effect a plurality of second fluid saturations that are successively decreased first fluid saturations, (g) determining the ratios of said measured resistivities along the selected length of said porous rock for each successively decreased first fluid saturation to the measured resistivity along the selected length of said porous rock for complete first fluid saturation, and (h) plotting the logarithm of said ratios against the logarithm of the corresponding partial first fluid saturations for which said ratios were determined.

5. A method for measuring the fluid distribution equilibrium of a porous rock comprising the steps of:

(a) injecting a first fluid into a porous rock to effect a first fluid saturation throughout said porous rock, (b) measuring resistivity along a selected length of said porous rock at said first fluid saturation, (c) injecting a second fluid which is immiscible with and of opposite electrical conductance with said first fluid into an end of said porous rock at an injection pressure to displace a portion of said first fluid from said porous rock and thereby effect a fluid saturation within said porous rock which is a partial saturation with respect to said first fluid saturation, (d) positioning a plurality of electrodes along the select length of said porous rock, spacings between said electrodes defining said subsections, (e) determining the lengths of said subsections, (f) determining the cross sectional area of said subsections, (g) passing a current through the select length of said porous rock, (h) measuring the voltage between each adjacent pair of electrodes, (i) determining the resistivity of each subsection from the measured voltage across the pair of electrodes defining the subsection, the current through the select length of porous rock, the measured length of the subsection, and the determined cross-sectional area of the porous rock, (j) subtracting the measured resistivities of adjacent pairs of said subsections to determine a resistivity gradient for each of said pairs of subsections, and (k) identifying the distribution of said first and second fluids within said homogeneous porous rock to be in equilibrium when the determined resistivity gradient between each of said pairs of subsections is zero.

* * * * *